(12) United States Patent
Wang et al.

(10) Patent No.: US 11,884,946 B2
(45) Date of Patent: Jan. 30, 2024

(54) GENERATION OF STABLE PROTEIN FILMS USING FLUOROUS SOLVENT

(71) Applicant: University of Massachusetts, Boston, MA (US)

(72) Inventors: Li-Sheng Wang, Taichung (TW); Sanjana Gopalakrishnan, Mumbai (IN); Vincent M. Rotello, Amherst, MA (US)

(73) Assignee: University of Massachusetts, Boston, MA (US)

( * ) Notice: Subject to any disclaimer, the term of this patent is extended or adjusted under 35 U.S.C. 154(b) by 143 days.

(21) Appl. No.: 16/180,260

(22) Filed: Nov. 5, 2018

(65) Prior Publication Data

US 2019/0136214 A1    May 9, 2019

Related U.S. Application Data

(60) Provisional application No. 62/582,151, filed on Nov. 6, 2017.

(51) Int. Cl.
*C07K 14/765* (2006.01)
*C12N 9/36* (2006.01)
(Continued)

(52) U.S. Cl.
CPC ............ *C12N 9/2462* (2013.01); *A61L 27/22* (2013.01); *A61L 27/34* (2013.01); *A61L 31/10* (2013.01);
(Continued)

(58) Field of Classification Search
CPC ...... C08L 89/00; C08L 33/08; C08L 2666/02; C08L 2203/16; C08L 2201/54; C08L 83/04; C08L 27/12; C08L 83/08; C08L 65/00; C08L 83/16; C08L 51/003; C08L 27/20; C08L 53/025; C08L 2205/04; C08L 23/02; C12N 2533/30; C12N 2330/31; C12Q 2563/149; A61L 26/0076; A61L 27/025; A61L 27/10; A61L 27/50; A61K 2800/28; A61K 8/25; A61K 8/345; A61K 6/20; A61K 9/0024; A61K 2800/87; A61K 8/895; A61K 8/585; A61K 2800/412;
(Continued)

(56) References Cited

U.S. PATENT DOCUMENTS 10,073,340 B2 * 9/2018 Rotello ................. C12N 11/14
2002/0006534 A1 * 1/2002 Wilkinson ........ H01M 8/04029
429/410

(Continued)

OTHER PUBLICATIONS

Jeoung et al. Fabrication of Robust Protein Films Using Nanoimprint Lithography. Adv Mater. Oct. 28, 2015;27(40):6251-5. (Year: 2015).*

(Continued)

Primary Examiner — Aradhana Sasan
Assistant Examiner — Jia-Hai Lee
(74) Attorney, Agent, or Firm — Schwegman Lundberg & Woessner, P.A.

(57) ABSTRACT

Methods of preparing protein films in the presence of organofluorine compounds are provided that can produce protein films that retain the solution phase characteristics of the proteins. The protein films can be coatings for medical devices.

17 Claims, 12 Drawing Sheets
(9 of 12 Drawing Sheet(s) Filed in Color)

(51) Int. Cl.
*A61L 31/10* (2006.01)
*A61L 27/22* (2006.01)
*C08L 89/00* (2006.01)
*C08H 1/00* (2006.01)
*A61L 27/34* (2006.01)

(52) U.S. Cl.
CPC .............. *C07K 14/765* (2013.01); *C08H 1/00* (2013.01); *C08L 89/00* (2013.01)

(58) Field of Classification Search
CPC ........ A61K 8/90; A61K 47/42; A61K 8/0241; A61K 2800/594; A61K 49/226; A61K 8/91; A61K 9/5052; A61K 9/5138; A61K 51/04; A61K 2800/52; A61K 2800/54; A61K 2800/596; A61K 2800/61; A61K 2800/612; A61K 8/64; A61K 8/69; A61K 47/65; A61K 51/088; A61K 6/887; C08J 2389/00; C08J 5/18; C08J 2201/04; C08J 2201/0542; C08J 2207/10; C08J 3/03; C08J 3/09; C08J 3/246; C08J 9/26; C09D 189/00; C09D 183/08; C09D 5/1693; A01N 63/00; A01N 63/30; A01N 25/00; A01N 25/26; A01N 59/00; H01L 24/32; H01L 24/83; H01L 21/67098; H01L 21/02315; H01L 21/02603; H01L 21/02639; H01L 21/02642; H01L 21/76814; H01L 2224/8385; H01L 27/14692; H01L 29/04; H01L 29/1608; H01L 31/049; H01L 33/60; H01L 39/128; H01L 39/2425; H01L 39/2469; H01L 51/5253; H01L 21/02019; H01L 21/02107; H01L 21/02282; C08F 14/18; C08F 230/08; C08F 214/18; C08F 283/12; C08F 2/00; C08F 259/08; C08F 30/08; C07C 21/18; Y10T 428/31663; Y10T 428/1352; Y10T 428/29; Y10T 428/2991; Y10T 442/2189; Y10T 442/2164; Y10T 442/2738; Y10T 442/2754; Y10T 137/0318; Y10T 428/24364; Y10T 428/2438; G01N 2001/028; G01N 1/405; B32B 2255/26; B32B 2037/243; B32B 2457/20; B32B 2457/202

See application file for complete search history.

(56) References Cited

U.S. PATENT DOCUMENTS

| | | | | |
|---|---|---|---|---|
| 2009/0269421 | A1* | 10/2009 | Ooya | A61P 29/00 424/649 |
| 2015/0152270 | A1* | 6/2015 | Aizenberg | B08B 17/025 210/500.27 |
| 2016/0096935 | A1* | 4/2016 | Rotello | C12N 11/14 435/177 |
| 2019/0136214 | A1* | 5/2019 | Wang | A61L 27/22 |

OTHER PUBLICATIONS

Sunny et al. Transparent antifouling material for improved operative field visibility in endoscopy. Proc Natl Acad Sci U S A. Oct. 18, 2016;113(42):11676-11681. (Year: 2016).*

Fujiwara et al. Transparent silicathin films prepared from sodium silicate and bovine serum albumin with petal effect. Ceramics International. 2015; 41: 7565-7572. (Year: 2015).*

Leslie et al. A bioinspired omniphobic surface coating on medical devices prevents thrombosis and biofouling. Nat Biotechnol. 2014; 32: 1134-1140. (Year: 2014).*

Gong et al. Fabrication of Super Hydrophobic Surfaces on Copper by Solution-immersion. Chinese Journal of Chemical Engineering. 2013; 21(8): 920-926. (Year: 2013).*

Sotiri et al. Immobilized liquid layers: A new approach to anti-adhesion surfaces for medical applications. Experimental Biology and Medicine 2016; 241: 909-918. (Year: 2016).*

* cited by examiner

COATED SCREW
INCUBATED WITH
BRILLIANT BLUE

COATED SCREW
INCUBATED WITH
BRILLIANT BLUE

GENERATION OF STABLE PROTEIN FILMS USING FLUOROUS SOLVENT

CROSS-REFERENCE TO RELATED APPLICATION

This application claims the benefit of priority to U.S. Provisional Patent Application Ser. No. 62/582,151, filed Nov. 6, 2017, the disclosure of which is incorporated herein in its entirety by reference.

STATEMENT OF GOVERNMENT SUPPORT

This invention was made with Government support under CHE-1740597 awarded by the National Science Foundation. The U.S. Government has certain rights in this invention.

BACKGROUND

Traditional heat curing methods for fabricating protein films can result in significant protein denaturation and hydrophobic surfaces.

SUMMARY OF THE INVENTION

In various embodiments, a method of making a protein film includes depositing a protein solution that includes one or more proteins on a substrate, to form a precursor protein film; and exposing the precursor protein film to at least one organofluorine compound, to form a protein film.

In various embodiments, a protein film is provided. The protein film includes one or more proteins that at least partially retain their secondary structure in the film, wherein the protein film includes intermolecular hydrophobic interactions between the proteins.

It has surprisingly been discovered that, in various embodiments, immersing substrates into a fluorous solution, minimizes protein rearrangement at the interface. Advantageously, in various embodiments, hydrophilic protein films can be generated on any substrate shape (e.g., planar or non-planar) using, for example, dip coating, and be stabilized using fluorous solvent. In various embodiments, the method is advantageously suitable for use with any types of protein, and consequently the method can generate films with different properties based on the choice of protein precursor. In various embodiments, the resulting protein films can be used for anti-fouling, anti-microbial, or controlled drug releasing surface coatings.

In various embodiments, the proteins in the film can at least partially retain their native structure, for example, secondary structure. In various embodiments, the stability and biodegradability of the protein film can be easily controlled. In various embodiments, the porosity of the protein film can be easily controlled, such as via addition of porogens to the film; such porous protein films can be used as biomembranes for controlled diffusion. In various embodiments, the protein film can have nanoscale features and patterns. In various embodiments, the protein film can include a non-fouling surface. For example, in various embodiments, the surface of the protein film can prevent macromolecule (e.g., protein) adsorption. In various embodiments, the resistance to macromolecule adsorption can make the protein film useful for coating implantable biomedical devices or for using as a surface treatment for marine equipment. In various embodiments, cellular adhesion can be easily regulated by using an appropriate protein. In various embodiments, the protein film can direct cellular growth in a nanoscale architecture. In various embodiments, the protein film can have favorable biocompatibility. In various embodiments, the protein film can have tissue engineering applications.

In various embodiments, small molecules can be incorporated into the protein film (e.g., antibiotics, halide ions such as chloride ions), augmenting functional behavior of the film. In various embodiments, the film can be used for controlled-release or delayed release of a small molecule incorporated into the film. In various embodiments, with appropriate loading of secondary components, or by chlorination of the proteins in the film (e.g., via amine groups), the protein film can be used as an antimicrobial surface coating agent (e.g., for catheters or other indwelling devices). In various embodiments, the protein film can respond rapidly to humidity changes (e.g., via color change). In various embodiments, the protein film can act as a matrix for controlled growth of nanoparticles.

BRIEF DESCRIPTION OF THE FIGURES

The patent or application file contains at least one drawing executed in color. Copies of this patent or patent application publication with color drawing(s) will be provided by the Office upon request and payment of the necessary fee.

The drawings illustrate generally, by way of example, but not by way of limitation, various embodiments of the present invention.

DETAILED DESCRIPTION OF THE INVENTION

Figure 1:
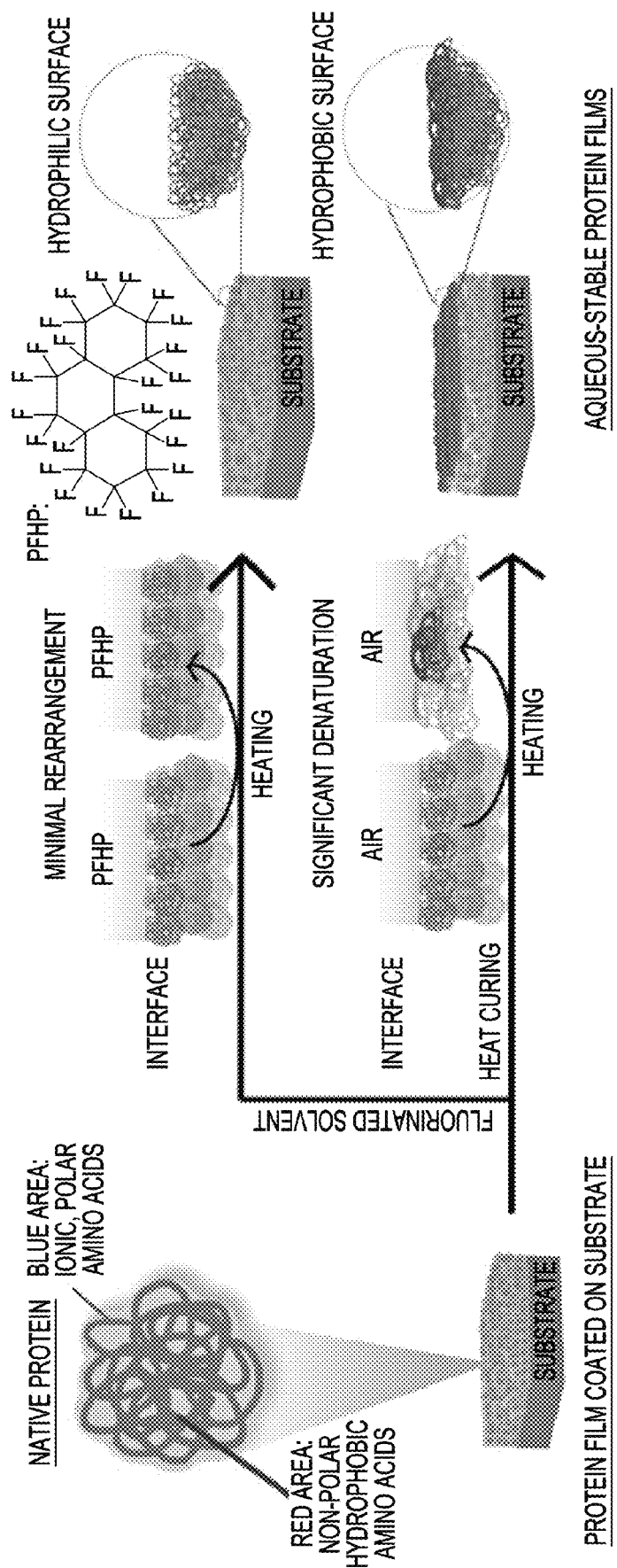
FIG. 1 illustrates methods for protein film fabrication, according to various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organofluorine compound," as used herein, refers to a substance containing carbon-fluorine bonds. The organofluorine compound can also contain one or more other atoms aside from carbon and fluorine, such as, for example, hydrogen, oxygen, nitrogen, sulfur, phosphorus, silicon, chlorine, bromine, iodine, and combinations thereof.

The term "perfluorinated hydrocarbon," as used herein, refers to a compound of carbon and hydrogen where every carbon-hydrogen bond has been replaced with a carbon-fluorine bond. The perfluorinated hydrocarbon can be saturated or unsaturated. When unsaturated, the perfluorinated hydrocarbon can have any number of carbon-carbon double bonds, and the double bonds can be cis-, trans-, or a mixture of cis- and trans-.

The term "halogen," as used herein, by themselves or as part of another substituent, means, unless otherwise stated, a fluorine, chlorine, bromine, or iodine atom.

The term "coating" as used herein refers to a continuous or discontinuous layer of material on the coated surface, wherein the layer of material can penetrate the surface and can fill areas such as pores, wherein the layer of material can have any three-dimensional shape, including a flat or curved plane. In one example, a coating can be formed on one or more surfaces, any of which may be porous or nonporous, by immersion in a bath of coating material.

The term "surface" as used herein refers to a boundary or side of an object, wherein the boundary or side can have any perimeter shape and can have any three-dimensional shape, including flat, curved, or angular, wherein the boundary or side can be continuous or discontinuous. While the term surface generally refers to the outermost boundary of an object with no implied depth, when the term 'pores' is used in reference to a surface, it refers to both the surface opening and the depth to which the pores extend beneath the surface into the substrate.

As used herein, the term "polymer" refers to a molecule having at least one repeating unit and can include copolymers.

Method of Making a Protein Film

In various embodiments, a method of making a protein film includes depositing a protein solution that includes one or more proteins on a substrate, to form a precursor protein film. The method also includes exposing the precursor protein film to at least one organofluorine compound, to form a protein film.

Various embodiments of the method include a precursor protein film of about 1 nm to about 100 microns thick. The precursor protein film can have a thickness of about 1 nm to about 100 microns, or about 100 nm to about 300 nm, or about 1 nm or less, or less than, equal to, or more than about 2 nm, 3, 4, 5, 10, 20, 25, 50, 100, 125, 150, 175, 200, 225, 250, 275, 500, 750 nm, 1 micron, 2, 3, 4, 5, 10, 20, 25, 50, 75, or about 100 microns.

Depositing of the protein solution on the substrate to form the precursor protein film can be any suitable depositing method. For example, the depositing can include printing, dipping, brushing, soaking, immersion, spraying, spin casting, or a combination thereof. For example, the depositing can include at least one of offset printing, screen printing, flexographic printing, inkjet printing, laser printing, dot matrix printing, daisy wheel printing, pad printing, relief printing, rotogravure printing, gravure printing, jet printing, ultrasonic spray printing, piezoelectric printing, spin casting, and three dimensional (3D) printing. In various embodiments, the depositing includes spin casting. The depositing can include evaporating or otherwise removing any suitable proportion of any one or more solvents from the protein solution to form the precursor protein film. In various embodiments, the depositing includes printing, dipping, brushing, soaking, immersion, spraying, spin casting, or a combination thereof.

The protein solution can include any one or more suitable proteins. The protein solution can be an aqueous protein solution. The one or more proteins can be any suitable proportion of the protein solution, such as about 0.01 wt % to about 99.9 wt %, about 1 wt % to about 20 wt %, about 5 wt % to about 15 wt %, or about 0.01 wt % or less, or less than, equal to, or more than about 0.1 wt %, 1, 2, 3, 4, 5, 6, 7, 8, 9, 10, 11, 12, 13, 14, 15, 16, 17, 18, 19, 20, 22, 24, 26, 28, 30, 35, 40, 45, 50, 55, 60, 65, 70, 75, 80, 85, 90, 95, 96, 97, 98, 99, 99.9, or about 99.99 wt % or more. The protein solution can include at least one of fibrous protein (e.g. cytoskeletal protein, extracellular matrix protein), a globular protein (e.g., plasma protein, coagulation factor, acute phase protein, hemoprotein, cell adhesion protein), a transmembrane transport protein (e.g., ion-pumping enzyme, ion channel protein, synport or antiport protein), a hormone or growth factor protein, a receptor protein, a DNA-binding protein, a transcription regulation protein, an immune system protein, a nutrient storage or transport protein, a chaperone protein, and an enzyme. In various embodiments, the protein solution includes at least one of anionic bovine serum albumin, neutral hemoglobin, and cationic lysozyme. In various embodiments, the protein solution can be substantially additive-free. In various embodiments, the protein solution can include one or more additional suitable components such as water-soluble polymers.

In various embodiments, the protein is a fibrous protein, a globular protein, a transmembrane transport protein, a hormone or growth factor protein, a receptor protein, a DNA-binding protein, a transcription regulation protein, an immune system protein, a nutrient storage or transport protein, a chaperone protein, an enzyme, or a combination thereof. In various embodiments, the protein is anionic bovine serum albumin, neutral hemoglobin, cationic lysozyme, or a combination thereof.

The substrate can be any suitable substrate, such that the method can be carried out as described herein. The substrate can be stiff or flexible. The substrate can also be substantially planar or non-planar. The substrate can be a plasma-cleaned substrate. In some examples, the substrate can include at least one of a silica wafer, glass, quartz, a polydimethylsiloxane, a medical device, and a polyester (e.g., Mylar). In various embodiments, the substrate can be cleaned prior to placing the protein solution there, such as via plasma-cleaning. In various embodiments, the substrate includes a silica wafer, glass, quartz, a polydimethylsiloxane, a polyester, a medical device, or a combination thereof.

The medical device can be any suitable medical device. Examples of medical devices include screws (e.g., dental or medical screws), catheters, stents, artificial joints, implants for the controlled-release of a therapeutic agents, orthopedic implants, wires, staples, surgical instruments, dental instruments, contact lenses, or any other type of three-dimensional object that can be used as a medical device. At least part of the surface of a medical device can be coated with the protein film. In various embodiments, substantially all of the surface of the medical device is coated with the protein film. The surface of the medical device can be a planar or non-planar (e.g., an irregular surface).

The organofluorine compound can, in some embodiments, contain carbon, fluorine, and 0 to 10 atoms (e.g., 0, 1, 2, 3, 4, 5, 6, 7, 8, 9, or 10 atoms) of any one of hydrogen, nitrogen, oxygen, sulfur, phosphorus, silicon, or another halogen, or combinations thereof. Suitable organofluroine compounds include, but are not limited to, 1,1,1,2,3,4,4,5,5,5-decafluoropentane heptacosafluorotributylamine, octadecafluorodecahydronaphthalene (cis, trans, or a mixture of cis and trans), octadecafluorooctane, pentadecafluorotriethylamine, perfluoro(methyldecalin), perfluorononane, perfluorooctane, tetradecafluorohexane, perfluoro(methylcyclohexane), perfluoro(methylcyclopentane), perfluoro-1,3-dimethylcyclohexane, perfluoro-1-octanesulfonyl fluoride, perfluoro-1,2-dimethylcyclohexane, perfluoro-1-butanesulfonyl fluoride, perfluoro(benzyltetralin), triphenylsulfonium perfluoro-1-butanesufonate, diphenyliodonium perfluoro-1-butanesulfonate, 1H,1H,2H-perfluoro-1-decene, 1H,1H,2H-perfluoro-1-hexene, 1H,1H,2H-perfluoro-1-octene, 1H,1H,2H,2H-perfluoro-1-octanol, 1H,1H,2H,2H-perfluoro-1-octanethiol 1H,1H,2H,2H-perfluoro-1-decanol, 1-Iodo-1H,1H,2H,2H-perfluorodecane, 1H,1H,2H,2H-perfluorodecanethiol, 1H,1H,2H,2H-perfluoro-1-decanethiol, 1H,1H,2H,2H-perfluoro-1-hexanethiol, tris(1,1,1,3,3,3-hexafluoro-2-propyl) phosphite, 1H,1H,2H,2H-perfluorooctyltriethoxysilane, hexadecafluoroheptane, 1H,1H,2H,2H-Perfluorodecyltriethoxysilane, 2,3,5,6-tetrafluoro-4-(trifluoromethyl)phenol, perfluoroperhydrophenanthrene, or combinations thereof. In various embodiments, the organofluorine compound is a perfluorinated compound. In various embodiments, the perfluorinated compound is a perfluorinated hydrocarbon. In various embodiments, the perfluorinated hydrocarbon is perfluoroperhydrophenanthrene (PFHP).

In various embodiments, the exposing includes heating the precursor protein film at a temperature of about 50° C. to about 200° C. The precursor protein film can be heated at a temperature of 60 to 200° C., 70 to 200° C., 80 to 200° C., 90 to 200° C., 100 to 200° C., 110 to 200° C., 120 to 200° C., 130 to 200° C., 140 to 200° C., 150 to 200° C., 160 to 200° C., 170 to 200° C., 120 to 190° C., 120 to 180° C., 120 to 170° C., 120 to 160° C., or 130 to 160° C. The precursor protein film can be heated at a temperature of less than, equal to, or greater than 50° C., 60° C., 70° C., 80° C., 90° C., 100° C., 110° C., 120° C., 130° C., 140° C., 150° C., 160° C., 170° C., 180° C., 190° C., or 200° C.

In various embodiments, the exposing includes immersing the precursor protein film in at least one organofluorine compound. Immersing can include at least some of the precursor protein film being immersed, such that at least some of the precursor protein film is covered by the organofluorine compound. The portion of the precursor protein film that is immersed in the organofluorine compound is not in direct contact with the air or atmosphere. The organofluorine compound that covers the precursor protein film so that the precursor protein film is not exposed to the air is, in various embodiments, in the liquid phase. In various embodiments, substantially all of the precursor protein film is immersed in the organofluorine compound. In various embodiments, the precursor protein film immersed in the organofluorine compound is heated at any of the temperatures described herein. The heating of the immersed precursor protein film can be performed in any suitable sealed container, or in a container open to the atmosphere.

In various embodiments, the precursor protein film is heated for about 1 minute to about 30 minutes. The precursor protein film can be heated for 5 to 30 minutes, 10 to 30 minutes, 15 to 30 minutes, 20 to 30 minutes, 10 to 25 minutes, 10 to 20 minutes, or less than, equal to, or greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes.

In various embodiments, the method further includes pressing the protein film with a mold. The mold can be made of any suitable material, such that the method can be carried out as described herein. In some embodiments, the mold can be a silane-functionalized or a siloxane mold, such as a fluorosilane-functionalized mold or a polydimethylsiloxane mold. Pressing the precursor film with the mold can be carried out in any suitable way. In some embodiments, pressing of the precursor film with the mold can include at least one of imprinting and embossing. Pressing the precursor film with a mold can include nanoimprint lithography (NIL), such as patterned nanoimprint lithography. In various embodiments, pressing the precursor protein film with a mold includes nanoimprint lithography.

In various embodiments, the protein film is about 1 nm to about 100 microns thick. The protein film can have a thickness of about 1 nm to about 100 microns, or about 100 nm to about 300 nm, or about 1 nm or less, or less than, equal to, or more than about 2 nm, 3, 4, 5, 10, 20, 25, 50, 100, 125, 150, 175, 200, 225, 250, 275, 500, 750 nm, 1 micron, 2, 3, 4, 5, 10, 20, 25, 50, 75, or about 100 microns.

In various embodiments, the protein film substantially prevents bacterial adhesion to the substrate. Prevention of bacterial adhesion can be useful, in various embodiments, as an anti-fouling coating. Without being bound by theory, in various embodiments, the prevention of bacterial adhesion is believed to arise from the hydrophilic nature of the protein film.

The method also includes, in various embodiments, growing one or more cells on the protein film. The cells can be any type cells, and the growing can be conducted in any suitable fashion. The protein film, in some embodiments, can be deposited in a pattern on the substrate. In some embodiments, the cells grown on the protein film substantially align with a pattern in the protein film, such as a pattern formed by the pressing of a mold on the precursor film or via other compressing techniques.

In various embodiments, the protein film is free of reaction products between the protein film and at least one organofluorine compound. When the precursor protein film is heated in the presence of at least one organofluorine compound, such as when the precursor protein film is heated while immersed in the organofluorine compound, no chemical interactions occur between at least one organofluorine compound and the protein film. The organofluorine compound, in some embodiments, acts as a chemically inert medium that protects the precursor protein film from reactions that can occur between proteins and air when heated, such as oxidation reactions.

The protein film can substantially retain the secondary structure of proteins in the protein solution, in various embodiments. Thus, even after heating, the protein film can retain the solution-phase properties of its constituent proteins, such as surface charge and degradability. The protein film can, in various embodiments, be subject to chemical reactions, such as digestion with a proteolytic enzyme when coating a substrate.

In various embodiments, a method of making a protein film includes depositing a protein solution comprising anionic bovine serum albumin on a substrate, to form a precursor protein film. The method also includes heating the precursor protein film immersed in PFHP at a temperature of about 140° C. to 200° C. for about 1 to 30 minutes, to form a protein film.

Protein Film

In various embodiments, a protein film is provided. The protein film includes one or more proteins that at least partially retain their secondary structure in the film, wherein the protein film includes intermolecular hydrophobic interactions between the proteins.

The protein film can have any suitable thickness. In various embodiments, the protein film can have a thickness of about 1 nm to about 100 microns, or about 100 nm to about 300 nm, or about 1 nm or less, or less than, equal to, or more than about 2 nm, 3, 4, 5, 10, 20, 25, 50, 100, 125, 150, 175, 200, 225, 250, 275, 500, 750 nm, 1 micron, 2, 3, 4, 5, 10, 20, 25, 50, 75, or about 100 microns.

The protein film can be substantially biocompatible, such that the protein film can safely come into contact with internal tissues for long periods such as on an implant surface.

The protein film can be substantially resistant to degradation in a solution including serum, such as any suitable serum at any suitable concentration.

The protein film can be substantially resistant to macromolecule adsorption, such as protein adsorption. The protein film can be substantially resistant to protein fouling.

In various embodiments, the protein film can include cells thereon. The cells can be substantially aligned with a pattern on the protein film. The protein film can coat at least a portion of the surface of any medical device described herein.

EXAMPLES

Various embodiments of the present invention can be better understood by reference to the following Examples which are offered by way of illustration. The present invention is not limited to the Examples given herein.

General.

Materials: BSA and Lyso were purchased from Fisher Scientific and used without further purification. Perfluoperhydrophenanthrene and tetradecafluorohexane were purchased from Sigma-Aldrich. Silica wafers were purchased from WRS Materials. Quartz microscopy slides were purchased from Electron Microscopy Sciences. MilliQ water was purified by using a Millipore water purification system. Dental implant screw was purchased from Alpha Bio Tec.

Film preparation: 10% w/w solutions of protein in MilliQ water were spin-coated at 3000 rpm for 25 seconds onto an oxygen plasma cleaned silicon substrate or quartz slides, yielding a thin film of protein.

Protein film stabilized by fluorous solvent: As prepared protein films were incubated in preheated perfluoperhydrophenanthrene solvent at 180° C. for 15 mins, following by washing with tetradecafluorohexane.

Protein film stabilized by Nanoimprint Lithography (NIL): Nanoimprinting of protein films was performed by using a Nanonex NX-2000 nanoimprinter with silicon molds. Imprinting was performed at various temperatures and pressures for 5 min. All molds were treated with heptadecafluoro-1,1,2,2-(tetrahydrodecyl) dimethylchlorosilane at 90° C. for 2 days in a vacuum chamber.

Kelvin probe force microscopy (KPFM): KPFM measurements were performed on a commercial AFM (Asylum Research MFP-3D; Santa Barbara, CA) using a Ti/Ir coated silicon tip (f~70 kHz; k~2 N/m (ASYELEC-01)) to probe the surface potential. During the measurement, the silicon substrate was kept at ground and the tip sequentially scanned along the top of each sample surface to collect the surface potential. All KPFM images were acquired at a scan rate of 0.6 Hz, a 3 VAC applied tip bias, and a 10 nm fixed separation between the tip and sample surface during the second pass.

3D coating: Dental implant screw was cleaned by oxygen plasma before dip coating with 20% w/w BSA solution. The screw was dried in a flame hood for 3 hours before heating in fluorous solvent. After washing with tetradecafluorohexane, the screw was dried by nitrogen gas.

Cell Culture: Mouse fibroblast cells 3T3 (ATCC CRL-1658) were cultured in Dulbecco's modified Eagle's medium (DMEM; ATCC 30-2002) supplemented with 10% bovine calf serum (ATCC 30-2030) and 1% antibiotics in T75 flasks. Cells were maintained at 37° C. in a humidified atmosphere of 5% CO2 and were sub-cultured once in 4 days.

Cell Adhesion: 3T3 cells grown in T75 flasks were washed with phosphate buffered saline (PBS), trypsinized with 1× trypsin and collected in DMEM media. Cells were centrifuged and were re-suspended in fresh DMEM media and counted by using a hemocytometer. Protein film coated surfaces were placed in a six-well plate where 3T3 cells were added to each well (100000 cells/well) and incubated for 48 h at 37° C. in a humidified atmosphere of 5% CO2.

Bacteria adhesion: DsRed-expressing *E. coli* bacteria were inoculated in 3 mL LB broth and grown to stationary phase at 37° C. The cultures were then diluted to O.D 0.1 in an M-9 media supplemented with 1 mM IPTG (isopropyl β-D-1-thiogalactopyranoside)0.30 2 mL of the dilution was poured onto the surfaces kept in 12 well culture plates. The surfaces were kept at 25° C. and the bacteria were allowed to grow for 24 hours. In general, the surfaces with bacteria were rinsed in deionized water three times before analysis under the microscope.

Characterization: Bright field images and fluorescence were detected by using an Olympus IX51 microscope with excitation wavelengths of 470 nm and 535 nm. AFM imaging of the surfaces was done on a Dimensions 3000 (Veeco) in tapping mode using a RTESP7 tip (Veeco). The film thickness of the protein films was measured by a Rudolph Research Auto EL ellipsometer. Far-UV circular dichroism (CD) spectra were measured on a JASCO J-720 spectropolarimeter with a quartz cuvette of 1 mm path length at 25° C. The spectra were recorded from 200 to 260 nm as an average of three scans at a rate of 20 nm/min. X-ray photoelectron spectroscopic (XPS) analysis was performed on a Physical Electronics Quantum 2000 spectrometer using a monochromatic Al Kα excitation at a spot size of 10 mm with pass energy of 46.95. Chemically distinct species were resolved using a Gaussian Lorentzian function with nonlinear least-squares fitting procedure.

Figure 2A:
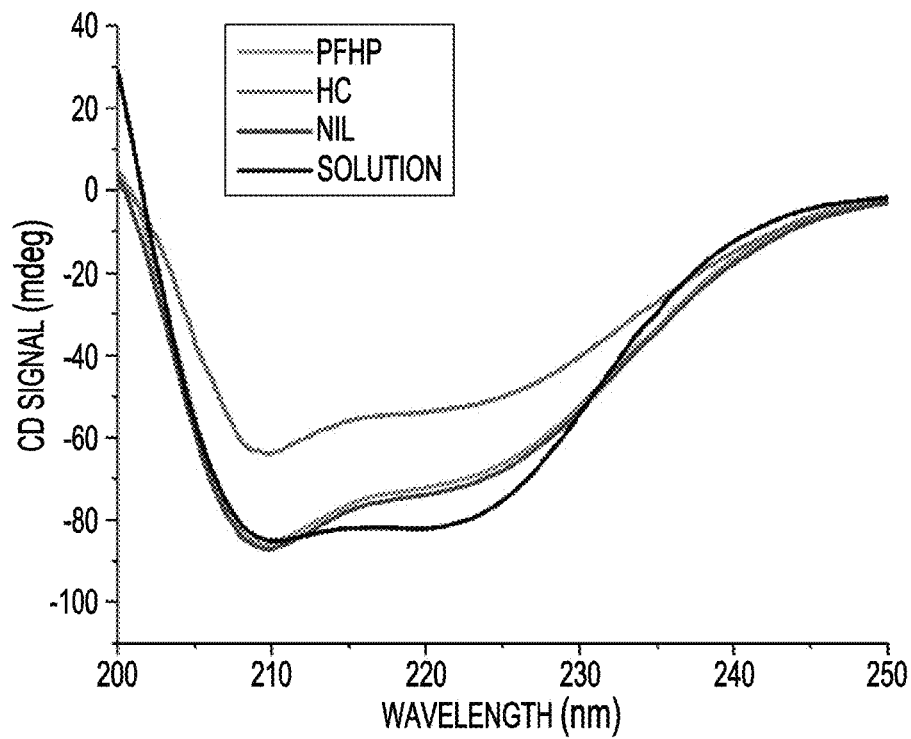
FIG. 2a shows the circular dichroism spectra of BSA (bovine serum albumin) in a phosphate buffer (solution), and BSA films prepared by heat-curing (HC) and stabilizing in perfluoroperhydrophenanthrene (PFHP).
Figure 2B:
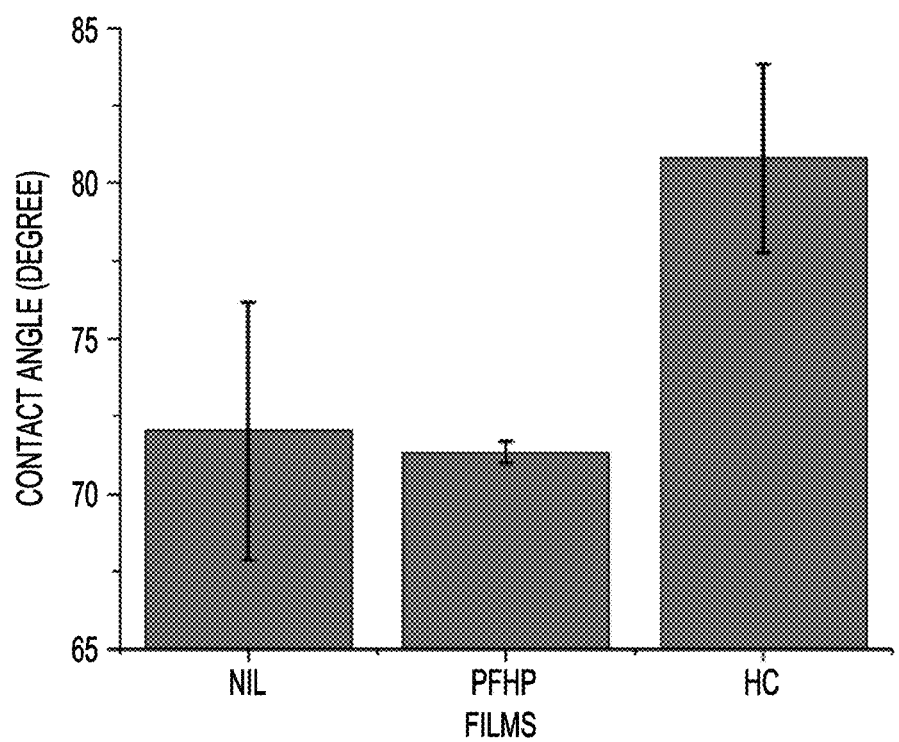
FIG. 2b shows the water contact angle on BSA films stabilized by PFHP and heat-curing methods.

Protein films of thickness of about 200 nm thickness were generated by spin-casting 10% w/w BSA solution onto plasma-cleaned substrates. These water-soluble films were next stabilized by heating at 180° C. in perfluoroperhydrophenanthrene (PFHP), or in air (FIG. 1). The secondary structure of protein building blocks in each film was characterized using circular dichroism spectroscopy. A substantial amount of the secondary structure was retained in films stabilized by PFHP. In contrast, protein films stabilized by traditional heat-curing (HC) resulted in massive loss of native structure (FIG. 2a). Protein denaturation can induce surface hydrophobicity, resulting in uncontrollable surface properties of protein films. The correlation between structure retention and surface hydrophobicity of protein films was deduced from the contact angle measurement. PFHP stabilization methods provide an inert fluorous environment during heating, which prevents protein rearrangement at the interface, leading to a relatively hydrophilic surface (FIG. 2b). On the other hand, protein building blocks likely denature and expose their hydrophobic regions at the protein-air interface during heat-curing, leading to a hydrophobic surface (FIG. 2b). The fluorous environment, in various embodiments, prevents proteins from significant denaturation while heating, thus enabling the fabrication of hydrophilic protein films.

Figure 2C:
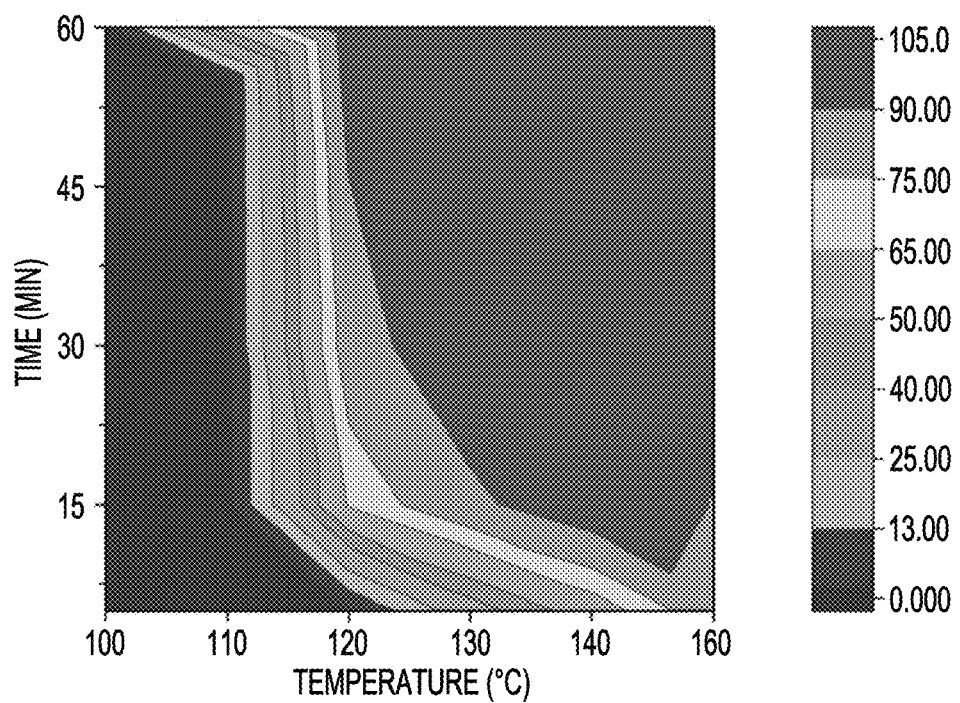
FIG. 2c is a heat map showing the effect of time and temperature on film stability in water. Films were washed for 1 min with water and the thickness measured by ellipsometry after drying.
Figure 2D:
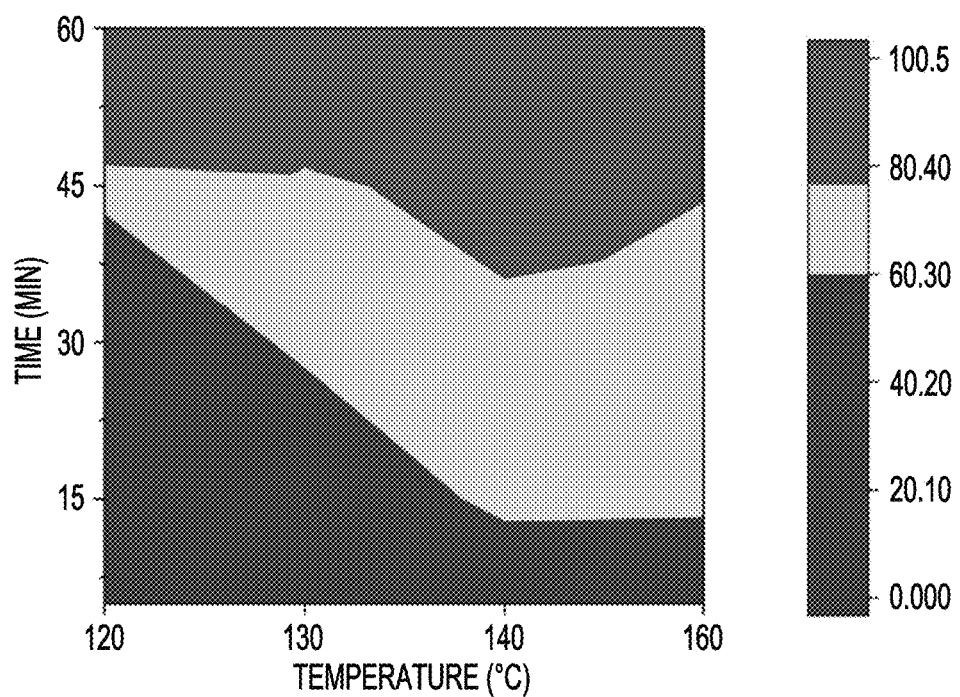
FIG. 2d is a heat map showing the effect of time and temperature on film hydrophilicity.

To study the dynamic range of the method in producing stable hydrophilic films, the processing temperature and time immersed in PFHP were varied to determine the conditions at which aqueous stability was achieved and hydrophilicity of protein films was maintained (FIG. 2c-d). In various embodiments, stable films were generated at temperatures >140° C. in 15 min when heating in PFHP. Stability can also be achieved at lower temperatures by prolonging the heating time. However, such films tend to be more hydrophobic owing to greater exposure to high temperatures (FIG. 2d).

Figure 3A:
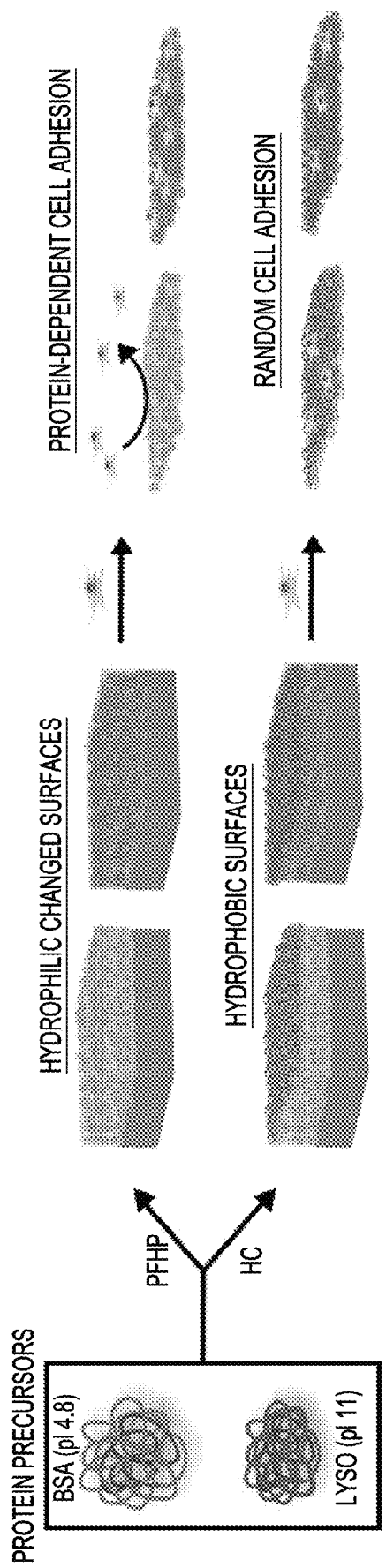
FIG. 3a is a surface potential of BSA and Lysozyme (LYSO) films fabricated by HC or PFHP method as determined by Kelvin probe force microscopy (KPFM).

The retention of protein structure and surface hydrophilicity of PFHP stabilized films implies that proteins' molecular properties, such as degradability and surface charge, can be imported into macroscopic films for different biomaterial applications. The biodegradability was demonstrated by incubating protein films with trypsin. Despite the protein films stabilized by PFHP were insoluble in aqueous, these stable protein films were still accessible by protease. In addition to the retention of biodegradability, the translation of surface charge into protein films was demonstrated using cationic lysozyme (LYSO, pI 11) and anionic BSA (pI 4.8) as protein precursors. The surface potential of resulting films was acquired using Kelvin Probe Force Microscopy (KPFM). The PFHP-LYSO surface exhibits a higher surface potential as compared to PFHP-BSA (FIG. 3a). The potential difference between PFHP-LYSO and PFHP-BSA is 2.8 V. In contrast, hydrophobic heat-cured films present a lower surface potential for both BSA and LYSO surfaces, and the difference between the surface potential is significantly smaller.

Figure 4A:
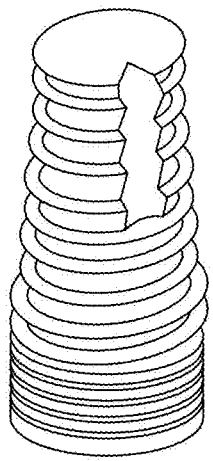
FIGS. 4a and 4b show images of bare and coated screws after staining with Brilliant blue, according to various embodiments.
Figure 4B:
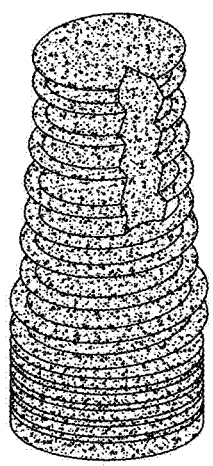
Figure 4C:
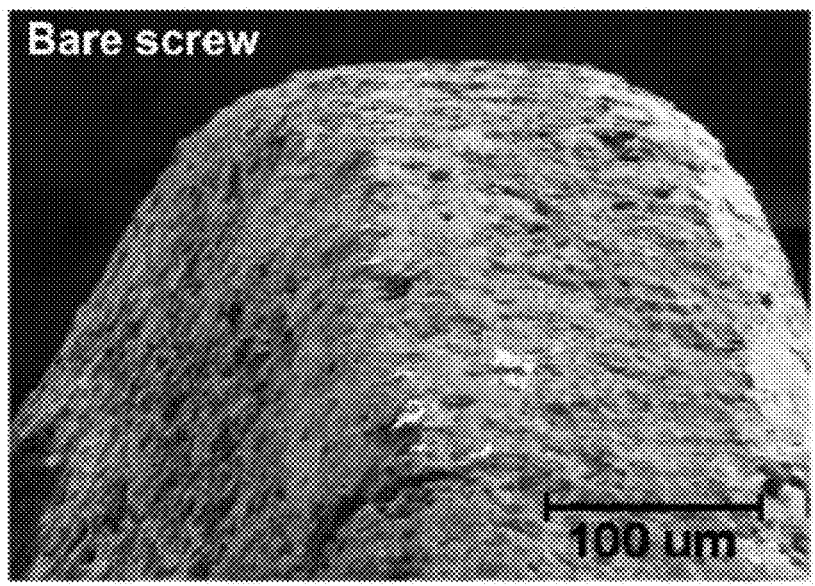
FIGS. 4c and 4d shows scanning electron microscopic images for bare and coated screw, according to various embodiments.
Figure 4D:
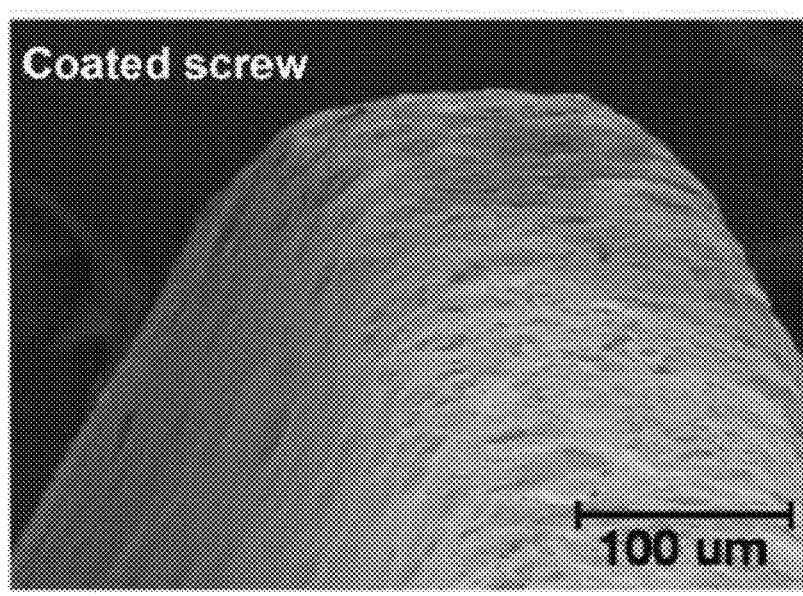
Figure 4E:
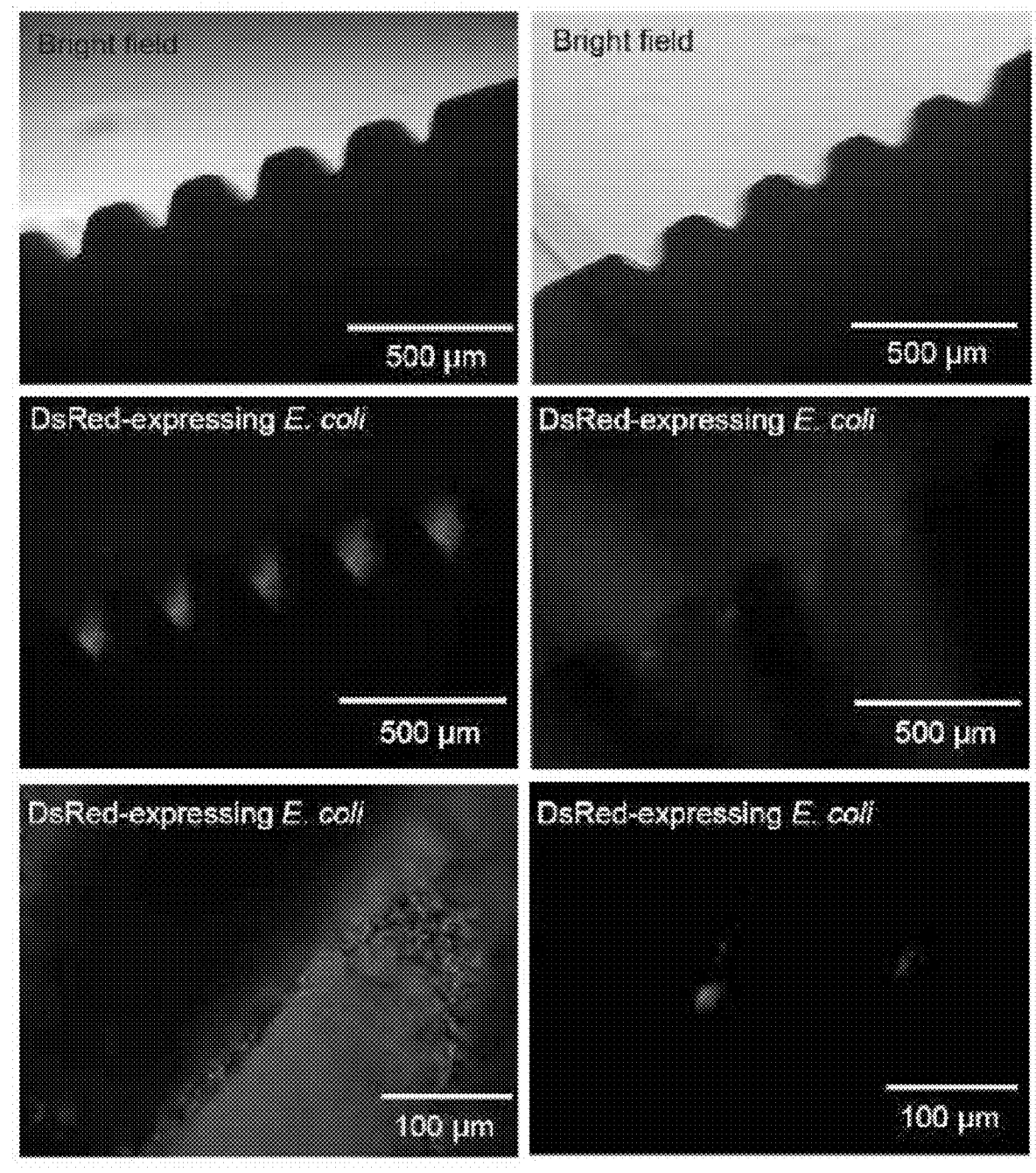
FIG. 4e shows optical and fluorescent microscopy images of DsRed-expressing E. coli on bare and coated screws after 24 hours of incubation, according to various embodiments.

Medical devices with complex geometries, such as dental and orthopedic implants, are often susceptible to bacterial contamination. Biocompatible protein films can be used as antifouling coatings on such implants. Based on the cellular adhesion studies, BSA was chosen to generate antifouling coating on dental implant screws as a functional demonstration. An oxygen plasma-cleaned screw was dip-coated with 20% w/w BSA solution, and the coated screw was then stabilized in PFHP. To verify that the coating was uniform and seamless, coated and uncoated screws were stained by incubating in a Brilliant Blue staining solution for 10 min. The protein film is prone to strong electrostatic interaction with Brilliant Blue resulting in a blue-colored screw after washing. In contrast, the bare screw showed no retention of Brilliant Blue after washing (FIGS. 4a and 4b). Another evidence of uniform coating was observed by scanning electron microscopy. The change in the topography of the screw from rough to smooth, is explained by the attachment of a thin layer of protein film on the coated screw (FIGS. 4c and 4d). The retention of functionality of the BSA film was demonstrated by incubating both bare and coated screws in DsRed-expressing *E. coli* for 24 hours. Fluorescence microscopy images show that the BSA-coated screw prevents bacteria adhesion almost uniformly throughout the screw while substantial amounts of *E. coli* were observed on the bare screw especially between the threads. These results demonstrate that the PFHP-stabilized protein films can be employed to generate anti-fouling BSA coatings on medical implants such as dental screws.

Example 1

Film Surface Properties

Figure 3B:
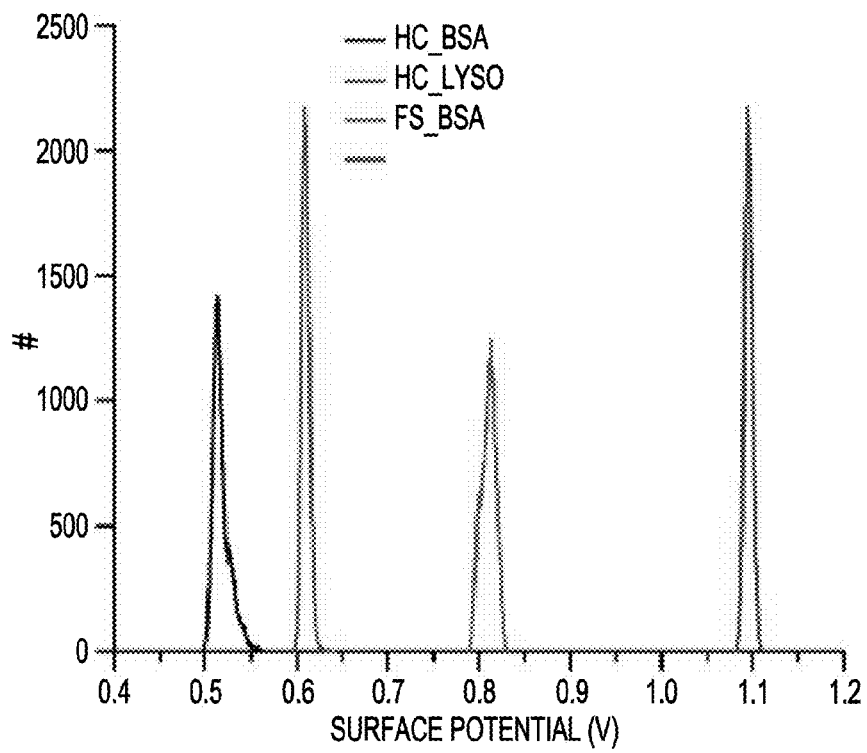
FIG. 3b shows the number of mammalian cells on protein films fabricated according to various embodiments and by HC methods

Different biomaterial applications require films with different surface properties. For example, positively charged surfaces promote cellular attachment, which can be employed for tissue engineering; zwitterionic or negatively charged surfaces are suitable for bio-inert coatings, especially for medical implants. Based on the method's ability of controlling surface potential of protein films, the functional demonstration of charged protein films was performed using cellular adhesion studies (FIG. 3). 3T3-L1 fibroblast cells were seeded onto the protein films for 24 hours and examined by microscopy after washing with PBS (FIG. 3b).

Figure 3C:
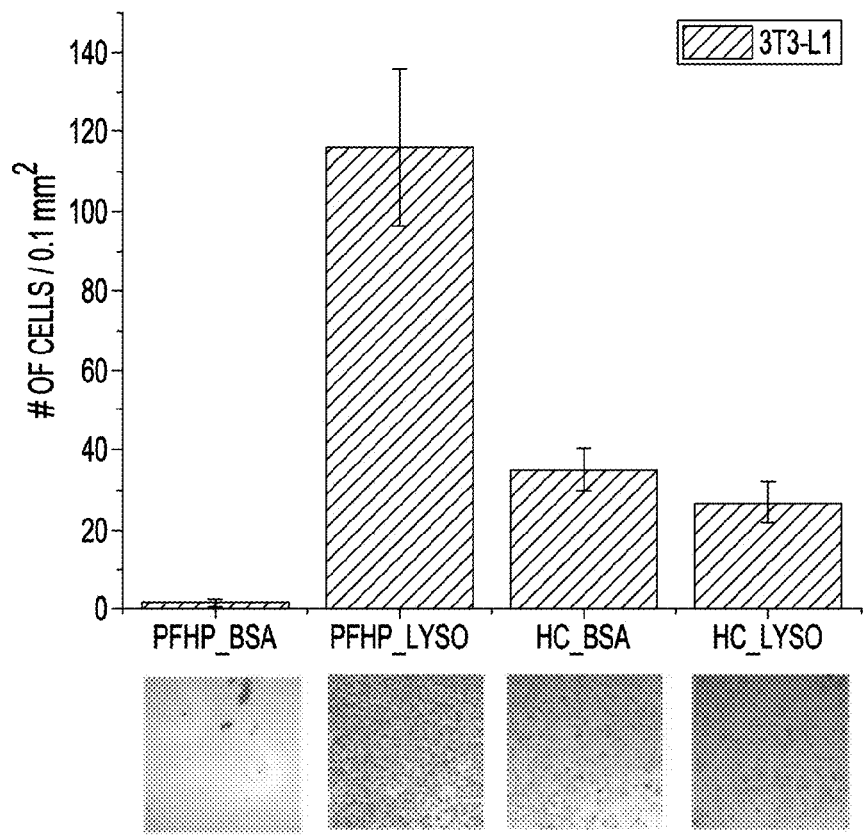
FIG. 3c shows bacterial cells adhered on protein films fabricated according to various embodiments and by HC methods.
Figure 3D:
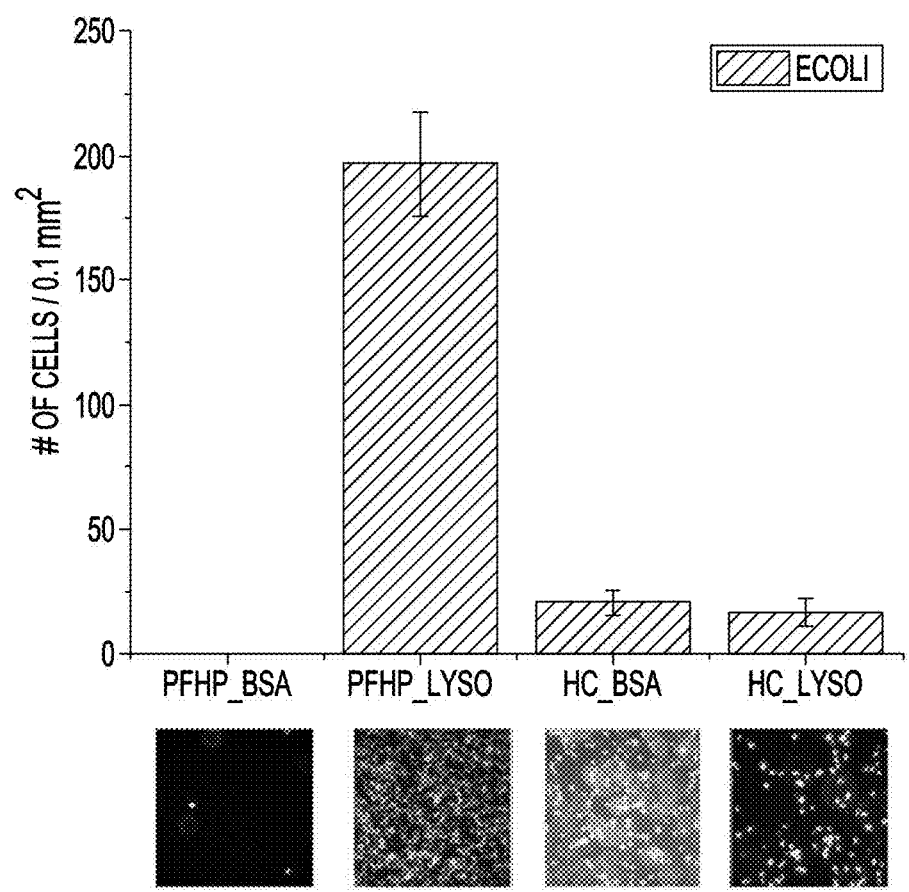
FIG. 3d shows bacterial cells adhered on protein films fabricated according to various embodiments and by HC methods.

PFHP-LYSO provided excellent adhesion for 3T3-L1, while PFHP-BSA showed exceptional anti-fouling property. Those results are in agreement with our previous observation of NIL films. In contrast, heat-cured films show no control of cellular adhesion, indicating the surface properties of protein precursors were lost during the stabilization process. In bacteria adhesion study, similar trend was observed (FIGS. 3c and 3d).

PFHP-BSA shows great resistance to bacterial fouling while PFHP-LYSO triggers a strong interaction with bacteria. These results, along with the contact angle studies, indicate the importance of the use of PFHP on retaining the surface hydrophilicity and consequently the capability of control over protein films properties.

Example 2

Dynamic Range of Perfluoro-Stabilized Films

Figure 5:
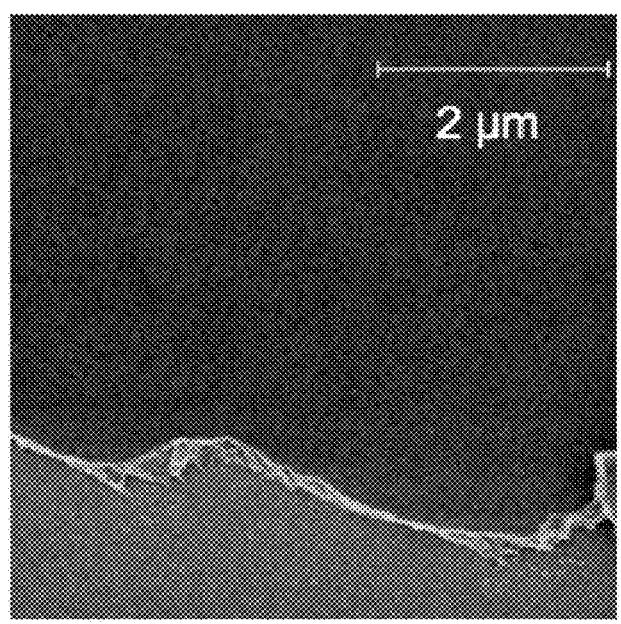
FIG. 5 illustrates a scanning electron microscopy image of a scratched protein film on Si wafer, in accordance with various embodiments.

Initial protein stabilization and denaturation studies focused on bovine serum albumin (BSA, an anionic protein). Protein films of thickness ~200 nm were generated by spin-casting 10% w/w BSA solution onto plasma-cleaned substrates (FIG. 5). These water-soluble films were next stabilized by heating at 180° C. in perfluoroperhydrophenanthrene (PFHP), air, or using NIL. The secondary structure of protein building blocks in each film was characterized using circular dichroism spectroscopy. Consistent with our prior studies, a substantial amount of the secondary structure was retained in films stabilized by PFHP and NIL. In contrast, protein films stabilized by traditional heat-curing (HC) resulted in massive loss of native structure (FIG. 2a). Protein denaturation can induce surface hydrophobicity, resulting in uncontrollable surface properties of protein films. The correlation between structure retention and surface hydrophobicity of protein films was deduced from the contact angle measurement. NIL and PFHP stabilization methods provide an inert fluorous environment during heating, which prevents protein rearrangement at the interface, leading to a relatively hydrophilic surface (FIG. 2b).

On the other hand, protein building blocks likely denature and expose their hydrophobic regions at the protein-air interface during heat-curing, leading to a hydrophobic surface (FIG. 2b). These results indicate that fluorous environment prevents proteins from significantly denaturing while heating, enabling the fabrication of hydrophilic protein films.

To study the dynamic range of PFHP method on producing stable hydrophilic films, the processing temperature and time in PFHP method were varied to determine the conditions at which aqueous stability was achieved and hydrophilicity of protein films was maintained (FIG. 2c-d). The results demonstrate that stable films were generated at temperatures >140° C. in 15 min when heating in PFHP.

Figure 6:
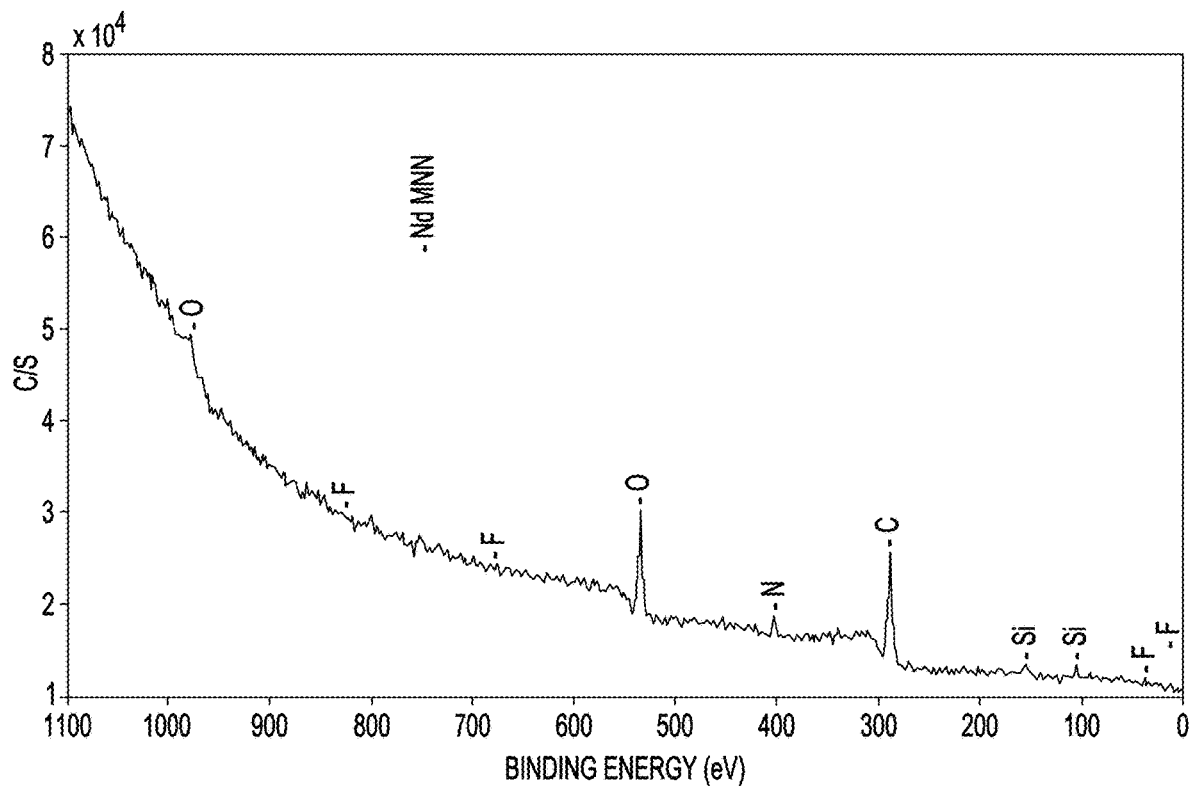
FIG. 6 shows an X-ray photoelectron spectrum of a protein film, in accordance with various embodiments. No fluorine residue is present in the protein film.

Additionally, no residue of fluorine was observed in protein films, even at the highest operating temperatures (FIG. 6), indicating that there is no chemical reaction occurred between fluorous solvent and protein films. Stability can also be achieved at lower temperatures by prolonging the heating time. However, such films tend to be more hydrophobic owing to greater exposure to high temperatures (FIG. 2d).

Example 3

Protein Structure Retention

Figure 7A:
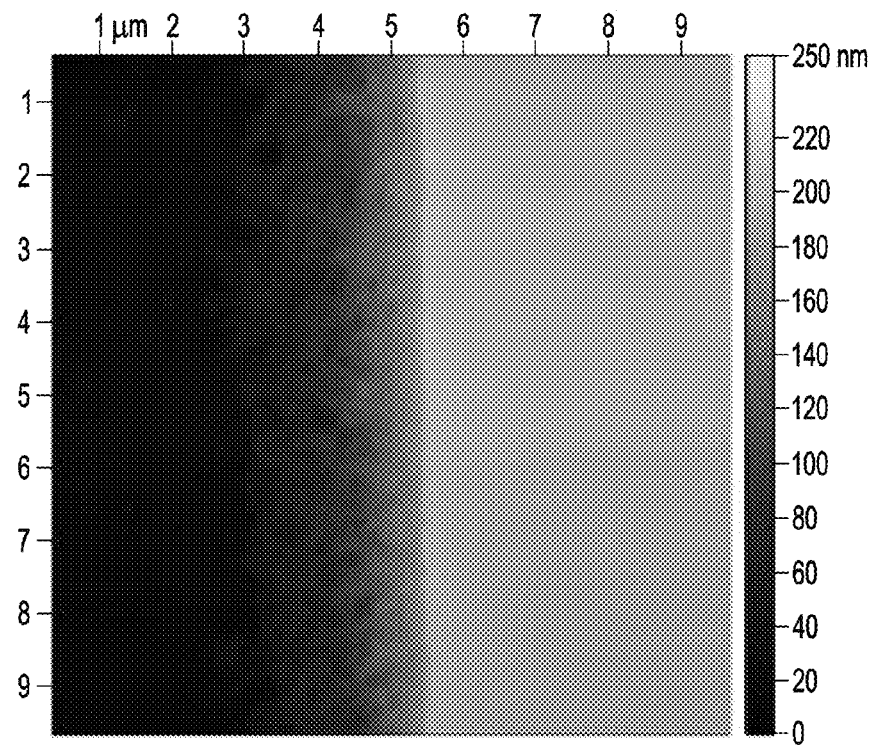
FIG. 7a is a topographic atomic force microscopy (AFM) image of a protein film in which the left-half of the film was incubated in 0.05% trypsin solution for 24 hours, according to various embodiments.
Figure 7B:
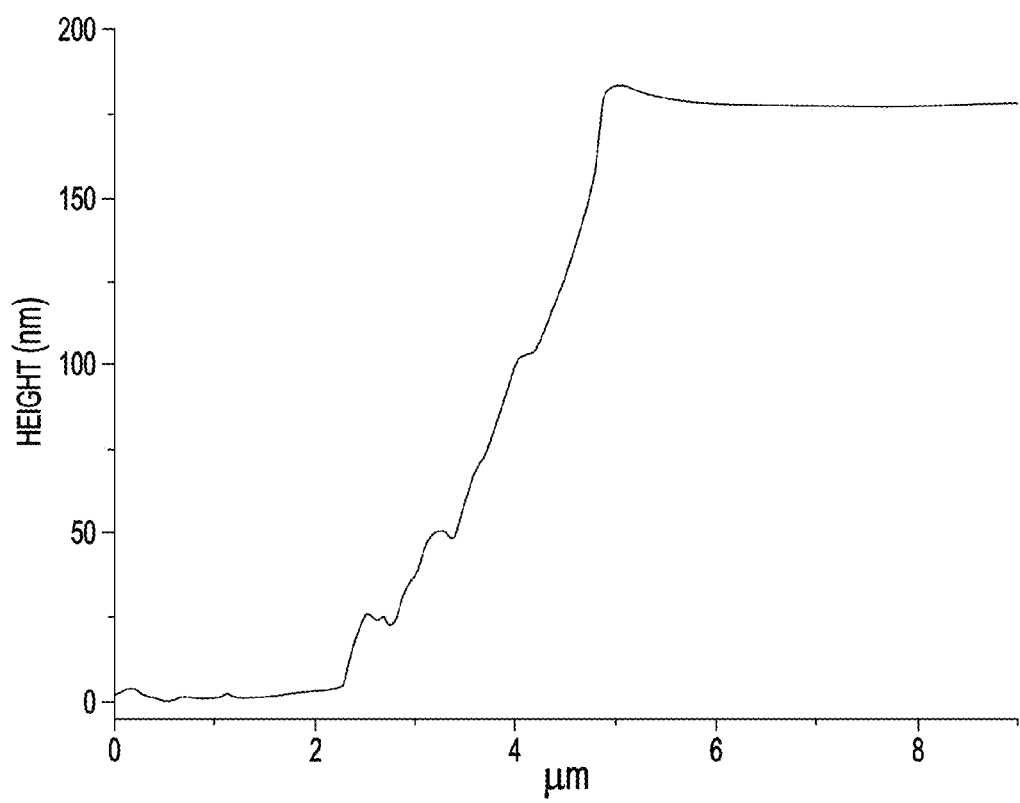
FIG. 7b is a cross-section of a protein film, imaged by AFM, in which the left-half of the film was incubated in 0.05% trypsin solution for 24 hours, according to various embodiments.
Figure 7C:
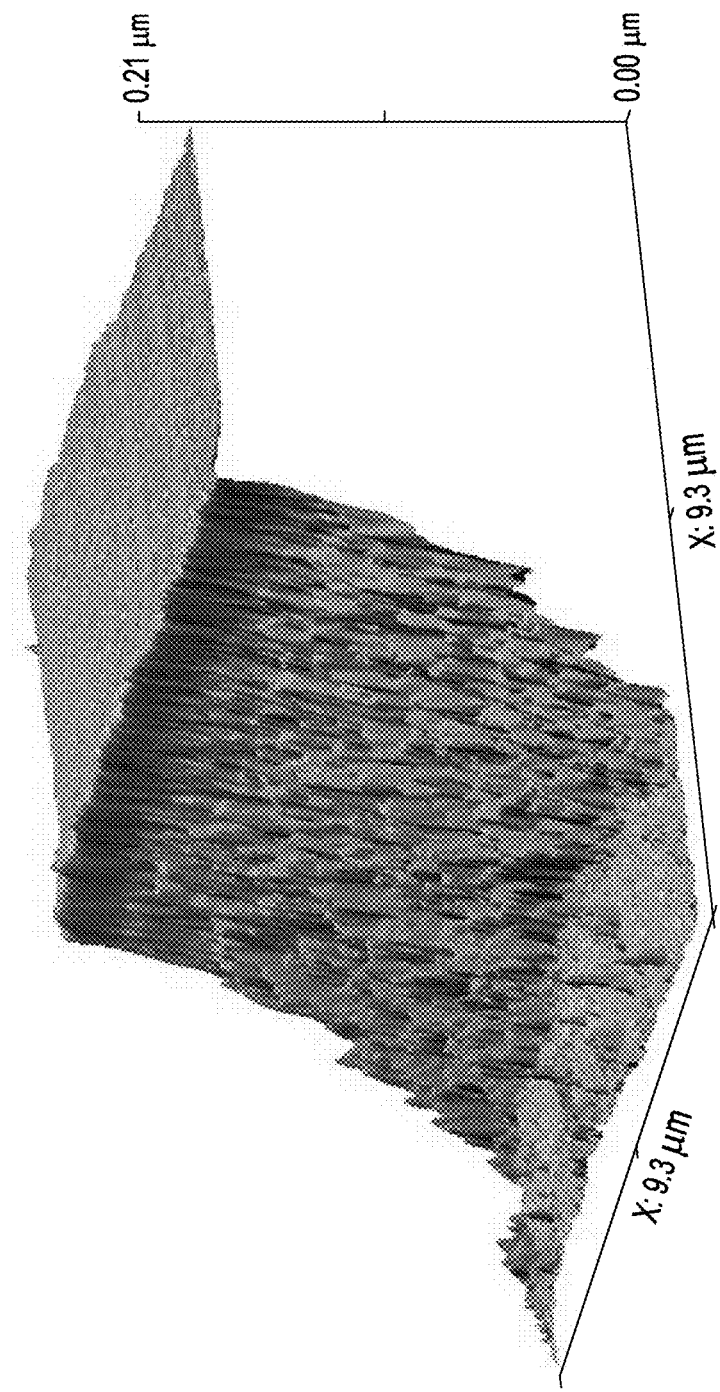
FIG. 7c is a 3D reconstruction of a protein film imaged by AFM, in which the left-half of the film was incubated in 0.05% trypsin solution for 24 hours, according to various embodiments.

The retention of protein structure and surface hydrophilicity of PFHP stabilized films implies that proteins' molecular properties, such as degradability and surface charge, can be imported into macroscopic films for different biomaterial applications. The biodegradability was demonstrated by incubating protein films with trypsin. Despite the protein films stabilized by PFHP were insoluble in aqueous, these stable protein films were still accessible by protease (FIGS. 7a-c).

In addition to the retention of biodegradability, the translation of surface charge into protein films was demonstrated using cationic lysozyme (LYSO, pI 11) and anionic BSA (pI 4.8) as protein precursors. The surface potential of resulting films was acquired using Kelvin Probe Force Microscopy (KPFM). The PFHP-LYSO surface exhibits a higher surface potential as compared to PFHP-BSA (FIG. 3a).

The potential difference between PFHP-LYSO and PFHP-BSA is 2.8 V, which remains consistent with our previous research with NIL films. In contrast, hydrophobic heat-cured films present a lower surface potential for both BSA and LYSO surfaces, and the difference between the surface potential is significantly lesser.

Example 4

Coating 3D Objects

The stabilization of protein films using PFHP provides a powerful technology for generating seamless protein coatings on three-dimensional (3D) substrates. Medical devices with complex geometry, like dental and orthopedic implants, are often susceptible to bacterial contamination. Protein films, being biocompatible, are viable candidates for anti-fouling coatings on such implants. Based on the cellular adhesion studies, BSA was chosen to generate antifouling coating on dental implant screws as a functional demonstration.

An oxygen plasma-cleaned screw was dip-coated with 20% w/w BSA solution, and the coated screw was then stabilized in PFHP. To verify that the coating was uniform and seamless, coated and uncoated screws were stained by incubating in a Brilliant Blue staining solution for 10 min. The protein film is prone to strong electrostatic interaction with Brilliant Blue resulting in a blue-colored screw after washing.

In contrast, the bare screw showed no retention of Brilliant Blue after washing (FIG. 4a). Other evidence of uniform coating included analysis by scanning electron microscopy. The change in the topography of the screw from rough to smooth, can be explained by the attachment of a thin layer of protein film on the coated screw (FIG. 4b). The retention of functionality of the BSA film was demonstrated by incubating both bare and coated screws in DsRed-expressing E. coli for 24 hours.

Fluorescence microscopy images show that the BSA-coated screw prevents bacteria adhesion almost uniformly throughout the screw while substantial amounts of E. coli were observed on the bare screw especially between the threads. These results demonstrate that the PFHP-stabilized protein films can be employed to generate anti-fouling BSA coatings on medical implants such as dental screws.

Example 5

To study the feasibility of forming protein films from proteins in addition to those already mentioned, films were made according to the methods described herein at Example 1, with the exception that the film included holo-transferrin, concanavalin A, hemoglobin, lipase, and collagen type 1. The films of Example 5 were stabilized in perfluoroperhydrophenanthrene (PFHP) at 170° C. for 15 min. Thickness change was measured before and after washing with water (n=3). Properties of the film including the molecular weight. of the film, the isoelectric point of the film (pI), the thickness change in the film, and the contact angle are presented in Table 1. The measured thickness change and contact angle for each film showed that each film maintained good stability in an aqueous environment and good surface hydrophilicity following PFHP treatment. This, coupled with the variety of proteins tested in the films, suggested that stable and hydrophilic films using almost any protein can be fabricated according to the methods of this disclosure.

TABLE 1

| Protein | M.W. (kDa) | pI value | Thickness change (%) | Contact angle (°) |
|---|---|---|---|---|
| holo-Transferrin | 76-81 | 5.2-6.3 | 102.07 ± 0.60 | 71.66 ± 2.87 |
| Concanavalin A | 104-112 | 4.5-5.5 | 105.53 ± 1.65 | 73.51 ± 2.67 |
| Hemoglobin | 64.5 | 6.8 | 102.91 ± 1.13 | 76.35 ± 2.12 |
| Lipase | 48 | 4.5-5.8 | 80.26 ± 2.69 | 75.90 ± 2.63 |
| Collagen type 1 | 115-130 | 9.3 | 91.05 ± 3.13 | 61.55 ± 0.88 |

Example 6

To further examine properties of the protein films, the percentage of film retained as well as the contact angle of the film following treatment was determined.

In this example, a protein film including bovine serum albumin and a film including a lysozyme were examined. To study the amount of film remaining post-treatment and the contact angle of the film, bovine serum albumin and lysozyme were treated with PFHP. The thickness ($t_1$) of the treated films were first measured through ellipsometry. Following this the films were washed with water for 1 min each and their thickness ($t_2$) were measured again. The percent of the film retained was calculated as $(t_1/t_2) \times 100$. FIG. 2a shows a region where stable bovine serum albumin films (e.g., >90% of the film) were retained post wash. FIG. 2b shows a region where stable lysozyme films (e.g., >90% of the film) were retained post wash.

Figure 8A:
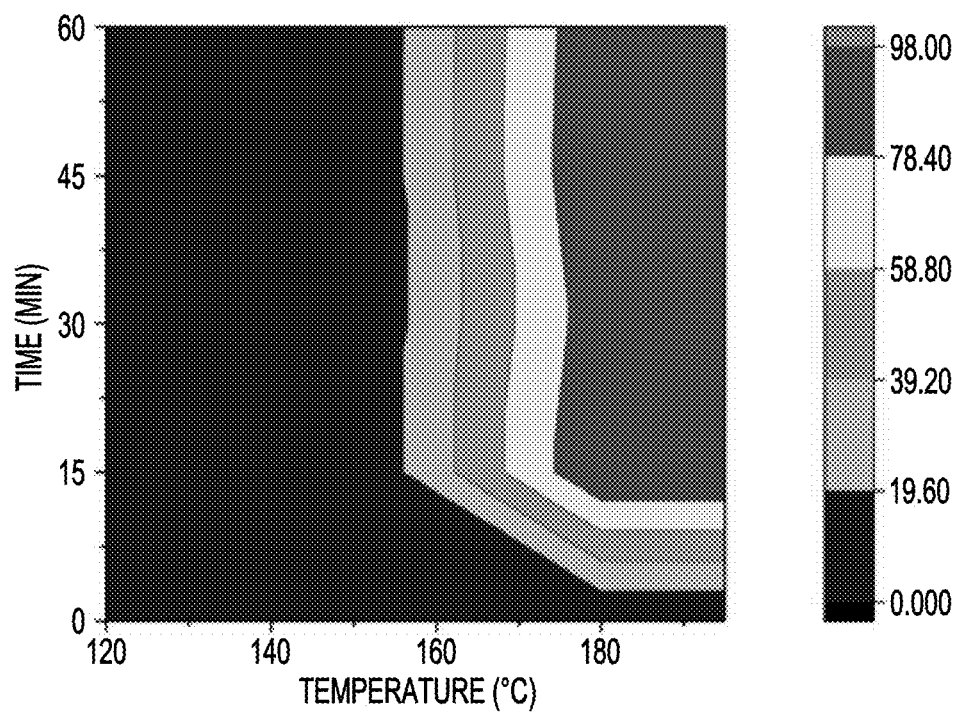
FIG. 8a is a plot showing the contact angle properties of a bovine serum albumin film remaining following treatment, in accordance with various embodiments.
Figure 8B:
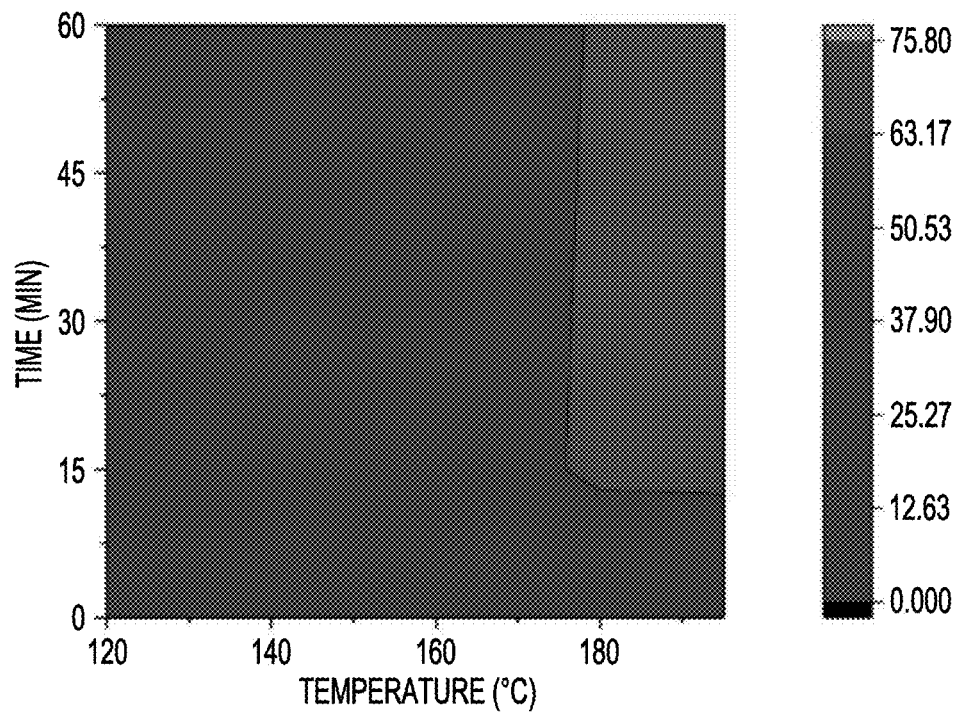
FIG. 8b is a plot showing the contact angle properties of a lysozyme film remaining following treatment, in accordance with various embodiments.

FIGS. 8a and 8b show the contact angle of water with the bovine albumin film and lysozyme film, respectively. The contact angle is a measure of the hydrophilicity of the film. The contact angle was measured by the static sessile drop method using 2 μl water droplets. The contact angle of a static droplet of water dropped onto the film was estimated through microscopic images of the water droplet. The films were considered hydrophilic if the contact angle was between 60° and 80° (angle values are shown in the spectrum to the side of the graphs).

The individual temperatures tested in this example were 100° C., 110, 120, 130, 140, and 180° C. for bovine serum albumin and 120, 140, 160 and 180° C. for lysozyme. The time durations tested were 5, 15, 30, 45 and 60 min at each of these temperatures.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Enumerated Embodiments

The following exemplary embodiments are provided, the numbering of which is not to be construed as designating levels of importance:

Embodiment 1 provides a method of making a protein film, the method comprising depositing a protein solution comprising one or more proteins on a substrate, to form a precursor protein film; and exposing the precursor protein film to at least one organofluorine compound, to form a protein film.

Embodiment 2 provides the method of embodiment 1, wherein the precursor protein film is about 1 nm to about 100 microns thick.

Embodiment 3 provides the method of any one of embodiments 1-2, wherein the depositing comprises printing, dipping, brushing, soaking, immersion, spraying, spin casting, or a combination thereof.

Embodiment 4 provides the method of any one of embodiments 1-3, wherein the protein solution is an aqueous protein solution, wherein the one or more proteins are about 0.01 wt % to about 99.9 wt % of the protein solution.

Embodiment 5 provides the method of any one of embodiments 1-4, wherein the protein is a fibrous protein, a globular protein, a transmembrane transport protein, a hormone or growth factor protein, a receptor protein, a DNA-binding protein, a transcription regulation protein, an immune system protein, a nutrient storage or transport protein, a chaperone protein, an enzyme, or a combination thereof.

Embodiment 6 provides the method of any one of embodiments 1-5, wherein the protein is anionic bovine serum albumin, neutral hemoglobin, cationic lysozyme, or a combination thereof.

Embodiment 7 provides the method of any one of embodiments 1-6, wherein the organofluorine compound is a perfluorinated compound.

Embodiment 8 provides the method of any one of embodiments 1-7, wherein the perfluorinated compound is a perfluorinated hydrocarbon.

Embodiment 9 provides the method of any one of embodiments 1-8, wherein the perfluorinated hydrocarbon is perfluoroperhydrophenanthrene (PFHP).

Embodiment 10 provides the method of any one of embodiments 1-9, wherein the exposing comprises heating the precursor protein film at a temperature of about 50° C. to about 200° C.

Embodiment 11 provides the method of any one of embodiments 1-10, wherein the exposing comprises immersing the precursor protein film in the at least one organofluorine compound.

Embodiment 12 provides the method of any one of embodiments 1-11, wherein the precursor protein film is heated for about 1 minute to about 30 minutes.

Embodiment 13 provides the method of any one of embodiments 1-12, wherein the method further comprises pressing the protein film with a mold.

Embodiment 14 provides the method of any one of embodiments 1-13, wherein pressing the precursor protein film with a mold comprises nanoimprint lithography.

Embodiment 15 provides the method of any one of embodiments 1-14, wherein the substrate comprises a silica wafer, glass, quartz, a polydimethylsiloxane, a polyester, a medical device, or a combination thereof.

Embodiment 16 provides the method of any one of embodiments 1-15, wherein substantially all of the surface of the medical device is coated with the protein film.

Embodiment 17 provides the method of any one of embodiments 1-16, wherein the protein film is about 1 nm to about 100 microns thick.

Embodiment 18 provides the method of any one of embodiments 1-17, wherein the protein film substantially prevents bacterial adhesion to the substrate.

Embodiment 19 provides the method of any one of embodiments 1-18, further comprising growing cells on the protein film.

Embodiment 20 provides the method of any one of embodiments 1-19, wherein the protein film is free of reaction products between the protein film and the at least one organofluorine compound.

Embodiment 21 provides the method of any one of embodiments 1-20, wherein the protein film substantially retains the secondary structure of proteins in the protein solution.

Embodiment 22 provides a method of making a protein film, the method comprising depositing a protein solution comprising anionic bovine serum albumin on a substrate, to form a precursor protein film; and heating the precursor protein film immersed in PFHP at a temperature of about 140° C. to 200° C. for about 1 to 30 minutes, to form a protein film.

Embodiment 23 provides a protein film comprising one or more proteins that at least partially retain their secondary structure in the film, wherein the protein film comprises intermolecular hydrophobic interactions between the proteins.

Embodiment 24 provides the method of any one of claims 1-22, wherein the substrate comprises a substantially non-planar surface.

What is claimed is:

1. A method of making a protein film on a substrate, the method comprising:
depositing a protein solution comprising one or more proteins on a substrate, to form the protein film on the substrate, wherein the one or more proteins are a fibrous protein, a globular protein, a transmembrane transport protein, a hormone or growth factor protein, a receptor protein, a DNA-binding protein, a transcription regulation protein, an immune system protein, a nutrient storage or transport protein, a chaperone protein, an enzyme, or a combination thereof;
immersing the protein film on the substrate in at least one organofluorine compound in liquid form that is chemically inert to the one or more proteins, and heating the at least one organofluorine compound to stabilize the protein film, wherein the stabilized protein film on the substrate retains the secondary structure of the one or more proteins in the protein solution;
removing the protein film on the substrate from immersion in the at least one organofluorine compound; and
washing the protein film on the substrate to remove any residual at least one organofluorine compound present following removal,
wherein the protein film on the substrate following removal from the immersion is a hydrophilic protein film and is free of any organofluorine compound and the organofluorine compound is optionally preheated ahead of immersion.

2. The method of claim 1, wherein the protein film is about 1 nm to about 100 microns thick.

3. The method of claim 1, wherein the depositing comprises printing, dipping, brushing, soaking, immersion, spraying, spin casting, or a combination thereof.

4. The method of claim 1, wherein the protein solution is an aqueous protein solution, wherein the one or more proteins are about 0.01 wt % to about 99.9 wt % of the protein solution.

5. The method of claim 1, wherein the protein is anionic bovine serum albumin, neutral hemoglobin, cationic lysozyme, or a combination thereof.

6. The method of claim 1, wherein the at least one organofluorine compound is a perfluorinated compound.

7. The method of claim 6, wherein the perfluorinated compound is a perfluorinated hydrocarbon.

8. The method of claim 7, wherein the perfluorinated hydrocarbon is perfluoroperhydrophenanthrene (PFHP).

9. The method of claim 1, wherein heating the at least one organofluorine compound comprises heating at a temperature of about 50° C. to about 200° C. to stabilize the protein film, followed by removal of the at least one organofluorine compound.

10. The method of claim 1, wherein the immersing comprises fully immersing the protein film in the at least one organofluorine compound.

11. The method of claim 1, wherein the method further comprises pressing the protein film on the substrate with a mold.

12. The method of claim 11, wherein pressing the protein film on the substrate with a mold comprises nanoimprint lithography.

13. The method of claim 1, wherein the substrate comprises a silica wafer, glass, quartz, a polydimethylsiloxane, a polyester, a medical device, or a combination thereof.

14. The method of claim 2, wherein the protein film is about 100 nm to about 300 nm thick.

15. The method of claim 1, wherein the substrate comprises a non-planar surface.

16. The method of claim 1, further comprising growing cells on the protein film.

17. A method of making a protein film on a substrate, the method comprising:
- depositing a protein solution comprising anionic bovine serum albumin on the substrate, to form a protein film on the substrate;
- dipping the protein film on the substrate in perfluoroperhydrophenanthrene (PFHP) and heating the PFHP while the substrate is immersed therein to maintain a temperature of about 140° C. to about 200° C. for about 1 to about 30 minutes, to stabilize the protein film on the substrate;
- removing the protein film on the substrate from immersion in the PFHP; and
- washing the protein film on the substrate to remove any residual at least one organofluorine compound present following removal,
- wherein the protein film on the substrate is a hydrophilic protein film and is free of the PFHP following the removal of the protein film on the substrate from the PFHP.

\* \* \* \* \*